United States Patent
Glombik et al.

(10) Patent No.: US 6,703,386 B2
(45) Date of Patent: Mar. 9, 2004

(54) DIPHENYLAZETIDINONE DERIVATIVES, PROCESS FOR THEIR PREPARATION, MEDICAMENTS COMPRISING THESE COMPOUNDS AND THEIR USE

(75) Inventors: Heiner Glombik, Hofheim (DE); Werner Kramer, Mainz-Laubenheim (DE); Stefanie Flohr, Eppstein (DE); Wendelin Frick, Hünstetten-Beuerbach (DE); Hubert Heuer, Schwabenheim (DE); Gerhard Jaehne, Frankfurt am Main (DE); Andreas Lindenschmidt, Bad Soden (DE); Hans-Ludwig Schaefer, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 39 days.

(21) Appl. No.: 10/021,044

(22) Filed: Dec. 19, 2001

(65) Prior Publication Data

US 2002/0128253 A1 Sep. 12, 2002

(30) Foreign Application Priority Data

Dec. 21, 2000 (DE) .......................................... 100 64 402
Nov. 7, 2001 (DE) .......................................... 101 54 518

(51) Int. Cl.[7] ................. C07D 227/087; A61K 31/444; A61P 3/06
(52) U.S. Cl. .................................. 514/210.02; 540/200
(58) Field of Search ...................... 514/210.02; 540/300

(56) References Cited

FOREIGN PATENT DOCUMENTS

| EP | 0 869 121 A1 | 10/1998 |
|---|---|---|
| WO | WO95/35277 | 12/1995 |
| WO | WO 97/26265 | 7/1997 |
| WO | WO 98/08871 | 3/1998 |
| WO | WO 99/03861 | 1/1999 |
| WO | WO00/20393 | 4/2000 |
| WO | WO00/20410 | 4/2000 |

OTHER PUBLICATIONS

"Ezetimibe—Hypolipidemic Cholesterol Absorption Inhibitor", Drugs of the Future, 25(7), pp. 679–685, (2000).
Hilgers et al., "Caco–2 Cell Monolayers as a Model for Drug Transport Across the Intestinal Mucosa", Pharmaceutical Research, 7(9), pp. 902–910, (1990).

Primary Examiner—Mark L Berch
(74) Attorney, Agent, or Firm—Finnegan, Henderson, Farabow, Garrett & Dunner, L.L.P.

(57) ABSTRACT

Compounds of the formula I, for example, are disclosed,

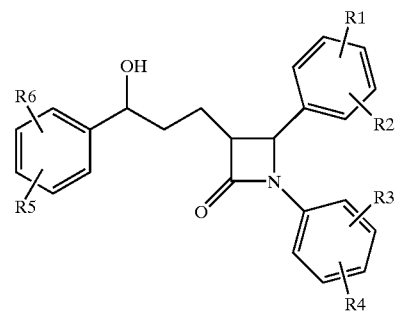

in which R1, R2, R3, R4, R5, and R6 independently of one another are $(C_0-C_{30})$-alkylene-L or are the meanings given in the description, and where L is shown connected to $(C_0-C_{30})$-alkylene as follows:

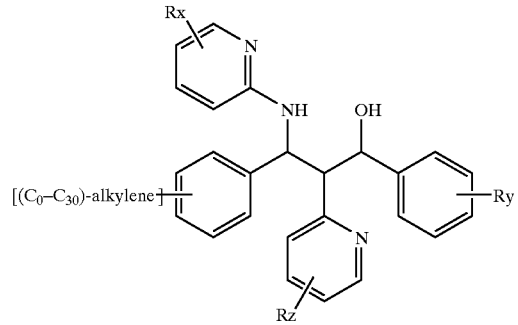

where Rx, Ry, Rz have the meanings given in the description, and their physiologically acceptable salts. The compounds are suitable for use, for example, as hypolipidemics.

11 Claims, No Drawings

DIPHENYLAZETIDINONE DERIVATIVES, PROCESS FOR THEIR PREPARATION, MEDICAMENTS COMPRISING THESE COMPOUNDS AND THEIR USE

This application claims the benefit of priority under 35 U.S.C. §119(a) to German patent application no. 10064402.3, filed on Dec. 21, 2000, and German patent application no. 10154518.5, filed on Nov. 7, 2001. The contents of both priority documents are incorporated by reference herein.

The invention relates to substituted diphenylazetidinones, to their physiologically acceptable salts and to derivatives having physiological function.

Diphenylazetidinones (such as, for example, ezetimibe) and their use for treating hyperlipidemia and arteriosclerosis and hypercholesterolemia have already been described [cf. Drugs of the Future 2000, 25(7):679–685].

It was an object of the invention to provide further compounds having a therapeutically utilizable hypolipidemic action. In particular, it was an object to find novel compounds which, compared to the compounds described in the prior art, are absorbed to a very low extent. Very low absorption is to be understood as meaning an intestinal absorption of less than 10%, preferably less than or equal to 5%. In particular, absorption of the novel compounds should be less than that of ezetimibe. Pharmaceutically active compounds which are absorbed to a very low extent generally have considerably fewer side-effects.

Accordingly, an embodiment of the invention relates to compounds of the formula I,

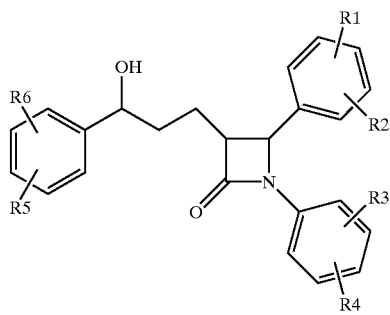

I in which
R1, R2, R3, R4, R5, R6 independently of one another are ($C_0$–$C_{30}$)-alkylene-L, where one or more carbon atoms of the alkylene radical may be replaced by —O—, —(C=O)—, —CH=CH—, —C≡C—, —N(($C_1$–$C_6$)-alkyl)- or —NH—; or H, F, Cl, Br, I, $CF_3$, $NO_2$, CN, COOH, COO($C_1$–$C_6$)-alkyl, $CONH_2$, CONH($C_1$–$C_6$)-alkyl, CON[($C_1$–$C_6$)-alkyl]$_2$, ($C_1$–$C_6$)-alkyl, ($C_2$–$C_6$)-alkenyl, ($C_2$–$C_6$)-alkynyl or O—($C_1$–$C_6$)-alkyl, where one, more or all hydrogens in the alkyl radicals may be replaced by fluorine; or $SO_2$—$NH_2$, $SO_2NH$—($C_1$–$C_6$)-alkyl, $SO_2N$[($C_1$–$C_6$)-alkyl]$_2$, S—($C_1$–$C_6$)-alkyl, S—$(CH_2)_n$-phenyl, SO—($C_1$–$C_6$)-alkyl, SO—$(CH_2)_n$-phenyl, $SO_2$—($C_1$–$C_6$)-alkyl or $SO_2$—$(CH_2)_n$-phenyl, where n=0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$; or $NH_2$, NH—($C_1$–$C_6$)-alkyl, N(($C_1$–$C_6$)-alkyl)$_2$, NH($C_1$–$C_7$)-acyl, phenyl or O—$(CH_2)_n$-phenyl, where n=0–6, where the phenyl ring may be mono- to trisubstituted by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$;

L is shown connected to ($C_0$–$C_{30}$)-alkylene as follows:

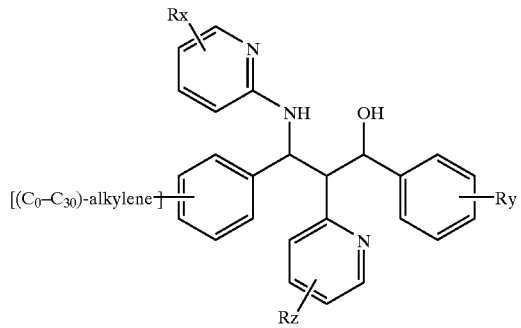

Rx, Ry, Rz independently of one another are H, F, Cl, Br, I, $CF_3$, $NO_2$, CN, COOH, COO—($C_1$–$C_6$)-alkyl, $CONH_2$, CONH—($C_1$–$C_6$)-alkyl, CON—[($C_1$–$C_6$)-alkyl]$_2$, ($C_1$–$C_6$)-alkyl, ($C_2$–$C_6$)-alkenyl, ($C_2$–$C_6$)-alkynyl or O—($C_1$–$C_6$)-alkyl, where one, more or all hydrogens in the alkyl radicals may be replaced by fluorine; or $SO_2$—$NH_2$, $SO_2NH$—($C_1$–$C_6$)-alkyl, $SO_2N$—[($C_1$–$C_6$)-alkyl]$_2$, S—($C_1$–$C_6$)-alkyl, S—$(CH_2)_n$-phenyl, SO—($C_1$–$C_6$)-alkyl, SO—$(CH_2)_n$-phenyl, $SO_2$—($C_1$–$C_6$)-alkyl or $SO_2$—$(CH_2)_n$-phenyl, where n=0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$; or $NH_2$, NH—($C_1$–$C_6$)-alkyl, N—(($C_1$–$C_6$)-alkyl)$_2$, NH—($C_1$–$C_7$)-acyl, phenyl or O—$(CH_2)$n-phenyl, where n=0–6, where the phenyl ring may be mono- to trisubstituted by F, Cl, Br, I, OH, $CF_3$, $NO_2$, CN, $OCF_3$, O—($C_1$–$C_6$)-alkyl, ($C_1$–$C_6$)-alkyl, $NH_2$, NH—($C_1$–$C_6$)-alkyl, N—(($C_1$–$C_6$)-alkyl)$_2$, $SO_2$—$CH_3$, COOH, COO—($C_1$–$C_6$)-alkyl or $CONH_2$;

wherein at least one of the radicals R1 or R6 has the meaning ($C_0$–$C_{30}$)-alkylene-L, where one or more carbon atoms of the alkylene radical may be replaced by —O—, —(C=O)—, —CH=CH—, —C≡C—, —N(($C_1$–$C_6$)-alkyl)- or —NH—, and its pharmaceutically acceptable salts.

Another embodiment of the invention relates to compounds of the formula I, in which at least one of the radicals R1 to R6 has the meaning ($C_0$–$C_{30}$)-alkylene-L, where one or more carbon atoms of the alkylene radical may be replaced by —O—, —(C=O)—, or —NH—.

Another embodiment of the invention relates to compounds of the formula I, in which one of the radicals R1 or R3 has the meaning ($C_0$–$C_{30}$)-alkylene-L, where one or more carbon atoms of the alkylene radicals may be replaced by —O—, —(C=O)— or —NH—.

Another embodiment of the invention relates to compounds of the formula I, in which one of the radicals R1 or R3 has the meaning —$(CH_2)_{0-1}$—NH—$(C=O)_{0-1}$—($C_3$–$C_{25}$)-alkylene-$(C=O)_{0-1}$—NH—L; where one or more carbon atoms of the alkylene radical may be replaced by oxygen atoms.

One of the radicals R1 to R6 may be linked, for example, to the L radical in the meta position of ring C of the L groups.

Owing to their increased solubility in water, compared to the parent compounds, pharmaceutically acceptable salts are particularly suitable for medical applications. These salts should have a pharmaceutically acceptable anion or cation. Suitable pharmaceutically acceptable acid addition salts of the compounds according to the invention are salts of inorganic acids, such as hydrochloric acid, hydrobromic acid, phosphoric acid, metaphosphoric acid, nitric acid, sulfonic acid and sulfuric acid, and of organic acids, such as acetic acid, benzenesulfonic acid, benzoic acid, citric acid, ethanesulfonic acid, fumaric acid, gluconic acid, glycolic acid, isothionic acid, lactic acid, lactobionic acid, maleic acid, malic acid, methanesulfonic acid, succinic acid, p-toluenesulfonic acid, tartaric acid and trifluoroacetic acid, for example. For medical purposes, very particular preference is given to using the chloride salt. Suitable pharmaceutically acceptable basic salts are ammonium salts, alkali metal salts (such as sodium and potassium salts) and alkaline earth metal salts (such as magnesium and calcium salts).

The scope of the invention also includes salts having a pharmaceutically unacceptable anion, which salts may be useful intermediates for preparing or purifying pharmaceutically acceptable salts and/or for use in nontherapeutic, for example in vitro, applications.

Here, the term "derivative having physiological function" refers to any physiologically acceptable derivative of a compound according to the invention, for example an ester, capable of forming, upon administration to a mammal, for example man, to form such a compound or an active metabolite (directly or indirectly).

A further aspect of this invention are prodrugs of the compounds according to the invention. Such prodrugs can be metabolized in vivo to give a compound according to the invention. These prodrugs may or may not be active in their own right.

The compounds according to the invention can also be present in various polymorphous forms, for example as amorphous and crystalline polymorphous forms. The scope of the invention includes all polymorphous forms of the compounds according to the invention, which form a further aspect of the invention. The compounds of the invention may also exist in the form of solvates.

The compounds of the formula I and their pharmaceutically acceptable salts, esters, prodrugs and derivatives having physiological function are ideal medicaments for treating an impaired lipid metabolism, in particular hyperlipidemia. The compounds of the formula I are also suitable for modulating the serum cholesterol concentration and for treating arteriosclerotic manifestations. The compounds of the invention are also suitable for the treatment of insulin resistance.

As used here, "treatment" or "therapy" of a condition and "treating" a condition can mean successfully eliminating the condition, reducing the effects associated with it, and/or reducing its severity. It also includes administering the relevant compounds to a patient to avoid recurrence of a condition. It also includes avoiding the onset of a condition by administering the relevant compounds to patients falling into a risk group or category for developing the particular condition. Those skilled in the art can routinely identify patients likely to present with a given condition, thereby qualifying as candidates for treatment.

The compound(s) of the formula (I) can also be administered in combination with other active compounds.

The amount of a compound of the formula (I) required to achieve the desired biological effect depends on a number of factors, for example on the specific compound chosen, on the intended use, on the mode of administration and on the clinical condition of the patient. In general, the daily dose is in the range from 0.1 mg to 100 mg (typically from 0.1 mg to 50 mg) per day per kilogram of bodyweight, for example 0.1–10 mg/kg/day. Tablets or capsules may contain, for example, from 0.01 to 100 mg, typically from 0.02 to 50 mg. In the case of pharmaceutically acceptable salts, the abovementioned weight data relate to the weight of the diphenylazetidinone-ion derived from the salt. For the therapy of the abovementioned conditions, the compounds of the formula (I) can be used themselves as the compound, but preferably they are present in the form of a pharmaceutical composition with an acceptable carrier. The carrier must of course be acceptable in the sense that it is compatible with the other constituents of the composition and is not harmful to the health of the patient. The carrier can be a solid or a liquid or both and is preferably formulated with the compound as an individual dose, for example as a tablet, which can contain from 0.05% to 95% by weight of the active compound. Further pharmaceutically active substances can also be present, including further compounds of the formula (I). The pharmaceutical compositions according to the invention can be prepared by one of the known pharmaceutical methods, which essentially consist in mixing the constituents with pharmacologically acceptable carriers and/or auxiliaries.

Pharmaceutical compositions according to the invention are those which are suitable for oral or peroral (e.g. sublingual) administration, although the most suitable manner of administration is dependent in each individual case on the nature and severity of the condition to be treated and on the type of the compound of the formula (I) used in each case. Coated formulations and coated delayed-release formulations are also included in the scope of the invention. Acid-resistant and enteric formulations are preferred. Suitable enteric coatings include cellulose acetate phthalate, polyvinyl acetate phthalate, hydroxypropylmethylcellulose phthalate and anionic polymers of methacrylic acid and methylmethacrylate.

Suitable pharmaceutical compounds for oral administration can be present in separate units, such as, for example, capsules, cachets, lozenges or tablets, which in each case contain a specific amount of the compound of the formula (I); as a powder or granules; as a solution or suspension in an aqueous or nonaqueous liquid; or as an oil-in-water or water-in-oil emulsion. As already mentioned, these compositions can be prepared according to any suitable pharmaceutical method which includes a step in which the active compound and the carrier (which can consist of one or more additional constituents) are brought into contact. In general, the compositions are prepared by uniform and homogeneous mixing of the active compound with a liquid and/or finely divided solid carrier, after which the product, if necessary, is shaped. For example, a tablet can thus be prepared by pressing or shaping a powder or granules of the compound, if appropriate with one or more additional constituents. Pressed tablets can be produced by tableting the compound in free-flowing form, such as, for example, a powder or granules, if appropriate mixed with a binder, lubricant, inert diluent and/or a (number of) surface-active/dispersing agent (s) in a suitable machine. Shaped tablets can be produced by shaping the pulverulent compound moistened with an inert liquid diluent in a suitable machine.

Pharmaceutical compositions which are suitable for peroral (sublingual) administration include lozenges which contain a compound of the formula (I) with a flavoring, customarily sucrose and gum arabic or tragacanth, and pastilles which include the compound in an inert base such as gelatin and glycerol or sucrose and gum arabic.

Suitable other active compounds for the combination preparations include: all antidiabetics, mentioned in Rote Liste 2001, Chapter 12, the disclosure of which is incorporated by reference herein. They can be combined with the compounds of the formula I according to the invention in particular to achieve a synergistically enhanced action. The active compound combination can be administered either by separate administration of the active compounds to the patient or in the form of combination preparations comprising a plurality of active compounds in a pharmaceutical preparation.

Antidiabetics include insulin and insulin derivatives, such as, for example, Lantus® or HMR 1964, GLP-1 derivatives, such as, for example, those disclosed by Novo Nordisk A/S in WO 98/08871, the disclosure of which is incorporated by reference herein, and oral hypoglycemic active compounds.

The oral hypoglycemic active compounds preferably include sulfonyl ureas, biguadines, meglitinides, oxadiazolidinediones, thiazolidinediones, glucosidase inhibitors, glucagon antagonists, GLP-1 agonists, potassium channel openers, such as, for example, those disclosed by Novo Nordisk A/S in WO 97/26265 and WO 99/03861, the disclosures of which are incorporated by reference herein, insulin sensitizers, inhibitors of liver enzymes involved in stimulating gluconeogenesis and/or glycogenolysis, modulators of glucose uptake, compounds which modulate lipid metabolism, such as antihyperlipidemic active compounds and antilipidemic active compounds, compounds which reduce food intake, PPAR and PXR agonists and active compounds which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor, such as, for example, ezetimibe, tiqueside, pamaqueside.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847.

In one embodiment of the invention, the compounds of the formula I are administered in combination with a fibrate, such as, for example, fenofibrate, clofibrate, bezafibrate.

In one embodiment of the invention, the compounds of the formula I are administered in combination with an MTP inhibitor, such as, for example, Bay 13-9952, BMS-201038, R-103757.

In one embodiment of the invention, the compounds of the formula I are administered in combination with a bile acid absorption inhibitor, such as, for example, HMR 1453.

In one embodiment of the invention, the compounds of the formula I are administered in combination with a CETP inhibitor, such as, for example, Bay 194789.

In one embodiment of the invention, the compounds of the formula I are administered in combination with a polymeric bile acid adsorber, such as, for example, cholestyramine, colesolvam.

In one embodiment of the invention, the compounds of the formula I are administered in combination with an LDL receptor inducer, such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein(a) antagonist, such as, for example, CI-1027 or nicotinic acid.

In one embodiment of the invention, the compounds of the formula I are administered in combination with a lipase inhibitor, such as, for example, Orlistat.

In one embodiment of the invention, the compounds of the formula I are administered in combination with insulin.

In one embodiment, the compounds of the formula I are administered in combination with a sulfonyl urea, such as, for example, tolbutamide, glibenclamide, glipizide or gliclazide.

In one embodiment, the compounds of the formula I are administered in combination with a biguanide, such as, for example, metformin.

In another embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone, or the compounds disclosed by Dr. Reddy's Research Foundation in WO 97/41097, the disclosure of which is incorporated by reference herein, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an active compound which acts on the ATP-dependent potassium channel of beta cells, such as, for example, tolbutamide, glibenclamide, glipizide, gliazide or repaglinide.

In one embodiment, the compounds of the formula I are administered in combination with more than one of the abovementioned compounds, for example in combination with a sulfonyl urea and metformin, a sulfonyl urea and acarbose, repaglinide and metformin, insulin and a sulfonyl urea, insulin and metformin, insulin and troglitazon, insulin and lovastatin, etc.

In a further embodiment, the compounds of the formula I are administered in combination with CART agonists, NPY agonists, MC4 agonists, orexin agonists, H3 agonists, TNF agonists, CRF agonists, CRF BP antagonists, urocortin agonists, β3-agonists, MSH (melanocyte-stimulating hormone) agonists, CCK agonists, serotonin reuptake inhibitors, mixed serotonin and noradrenergic compounds, 5HT agonists, bombesin agonists, galanin antagonists, growth hormone, growth hormone-releasing compounds, TRH agonists, decoupling protein 2- or 3 modulators, leptin agonists, DA agonists (bromocriptin, doprexin), lipase/amylase inhibitors, PPAR modulators, RXR modulators or TR-β agonists.

In one embodiment of the invention, the further active compound is leptin.

In one embodiment, the further active compound is dexamphetamine or amphetamine.

In one embodiment, the further active compound is fenfluramine or dexfenfluramine.

In another embodiment, the further active compound is sibutramine.

In one embodiment, the further active compound is Orlistat.

In one embodiment, the further active compound is mazindol or phentermine.

In one embodiment, the compounds of the formula I are administered in combination with fiber, preferably insoluble fiber, such as, for example, Caromax®. The combination with Caromax® can be given in one preparation or by separate administration of compounds of the formula I and Caromax®. Here, Caromax® can also be administered in the form of food, such as, for example, in bakery goods or muesli bars. Compared to the individual active compounds, the combination of compounds of the formula I with Caromax® is, in addition to an enhanced action, in particular with respect to the lowering of LDL cholesterol, also characterized by its improved tolerability.

It goes without saying that each suitable combination of the compounds according to the invention with one or more of the compounds mentioned above and optionally one or more further pharmacologically active substances is included in the scope of the present invention.

The invention furthermore provides both stereoisomer mixtures of the formula I and the pure stereoisomers of the formula I, and diastereomer mixtures of the formula I and the pure diastereomers. The mixtures are separated by chromatographic means.

Preference is given to both racemic and enantiomerically pure compounds of the formula I of the following structure:

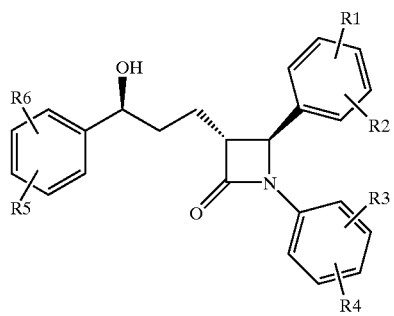

Preference is furthermore given to compounds of the formula I in which the L radicals have the following meaning:

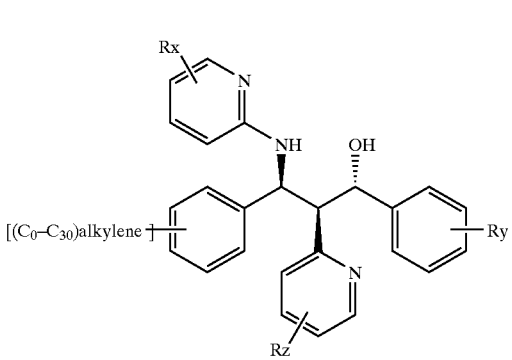

The invention furthermore provides a process for preparing the compounds of the formula I which comprises obtaining the compounds of the formula I by proceeding analogously to the reaction scheme below.

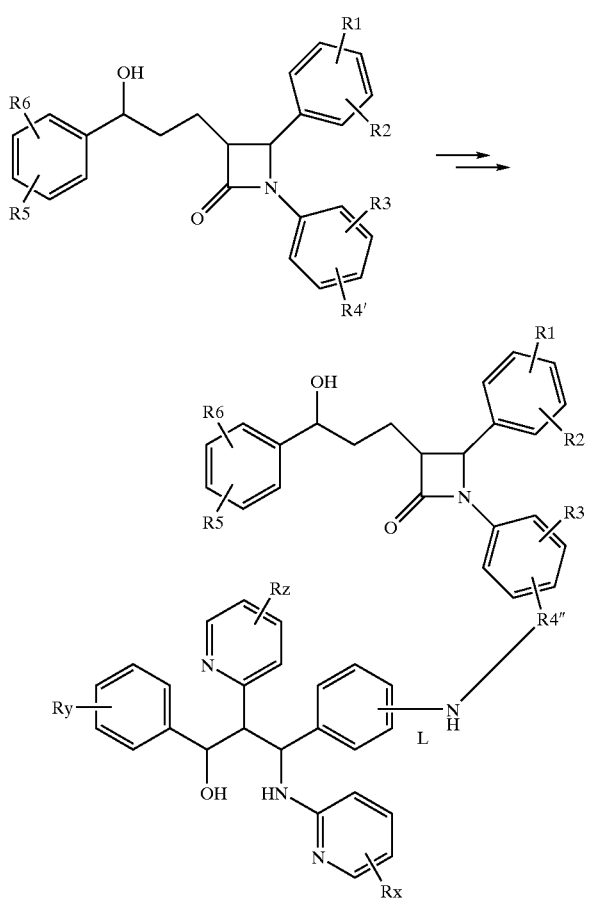

R4'' is $(C_0-C_{30})$-alkylene, where one or more carbon atoms of the alkylene radical may be replaced by —O—, —(C=O)—, —CH=CH—, —C≡C—, —N(($C_1-C_6$)-alkyl)- or —NH—.

Alternatively, the attachment to the L group is via ring A or C.

The examples below serve to illustrate the invention in more detail, without limiting the invention to the products and embodiments described in the examples.

EXAMPLE IV

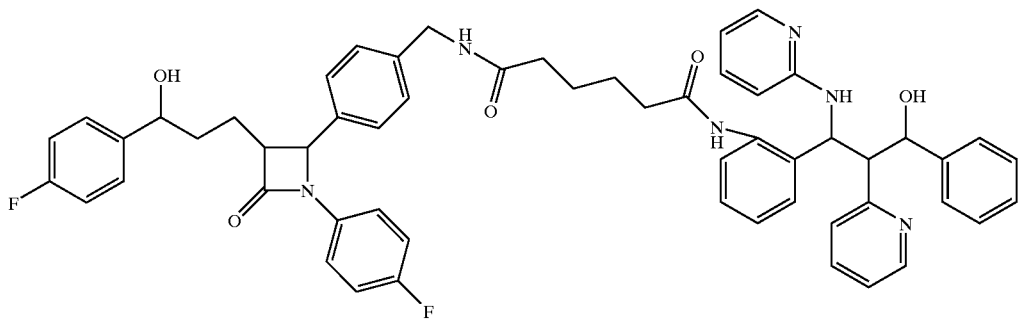

N-4-{1-(4-Fluorophenyl)-3-[3-(4-fluorophenyl)-3-hydroxypropyl]-4-oxoazetidin-2-yl}-benzyl-N'-{2-[3-hydroxy-3-phenyl-2-pyridin-2-yl-1-(pyridin-2-ylamino)propyl]phenyl}-hexanediamide (14)

a) 5-{2-[3-Hydroxy-3-phenyl-2-pyridin-2-yl-1-(pyridin-2-ylamino)propyl]phenylcarbamoyl}pentanoic acid (13)

Prepared from 1.5 g of 3-(2-aminophenyl)-1-phenyl-2-pyridin-2-yl-3-(pyridin-2-ylamino)propan-1-ol, 3.4 g of hexanedioic acid, 1.04 g of dicyclohexylcarbodiimide and 640 mg of benzotriazol-1-ol, analogously to example II f)

EXAMPLE XIII

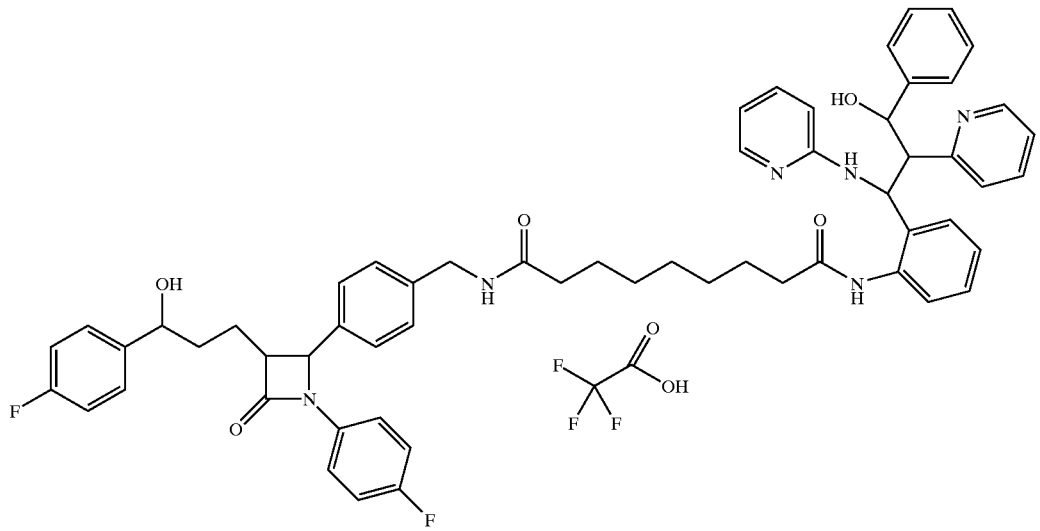

Product of molecular weight 524.6 ($C_{31}H_{32}N_4O_4$); MS (ESI+): 525 (M+H$^+$); (ESI−): 523 (M−H$^+$)

b) N-4-{1-(4-Fluorophenyl)-3-[3-(4-fluorophenyl)-3-hydroxypropyl]-4-oxoazetidin-2-yl}-benzyl-N'-{2-[3-hydroxy-3-phenyl-2-pyridin-2-yl-1-(pyridin-2-ylamino)propyl]phenyl}-hexanediamide (14)

Prepared from 300 mg of 4-(4-aminomethylphenyl)-1-(4-fluorophenyl)-3-[3-(4-fluorophenyl)-3-hydroxypropyl]azetidin-2-one, 372 mg of 5-{2-[3-hydroxy-3-phenyl-2-pyridin-2-yl-1-(pyridin-2-ylamino)propyl]phenylcarbamoyl}pentanoic acid, 155 mg of dicyclohexylcarbodiimide and 120 mg of benzotriazol-1-ol in 25 ml of tetrahydrofuran analogously to example III, chromatography: SiO$_2$, dichloromethane/methanol=10:1; product of molecular weight 929.1 ($C_{56}H_{54}F_2N_6O_5$); MS (ESI+): 929 (M+H$^+$).

(1-{2-[8-(4-{1-(4-Fluorophenyl)-3-[3-(4-fluorophenyl)-3-hydroxypropyl]-4-oxoazetidin-2-yl}benzylcarbamoyl)octanoylamino]phenyl}-3-hydroxy-3-phenyl-2-pyridin-2-yl-propyl)pyridin-2-yl-ammonium trifluoroacetate (27)

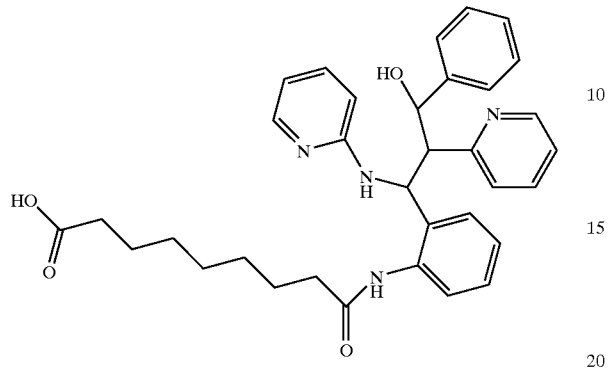

a) 8-{2-[3-Hydroxy-3-phenyl-2-pyridin-2-yl-1-(pyridin-2-ylamino)propyl]phenylcarbamoyl}octanoic acid (26)

$C_{34}H_{38}N_4O_4$ (566.72) MS (ESI) 567 (M+H)

EXAMPLE XIV

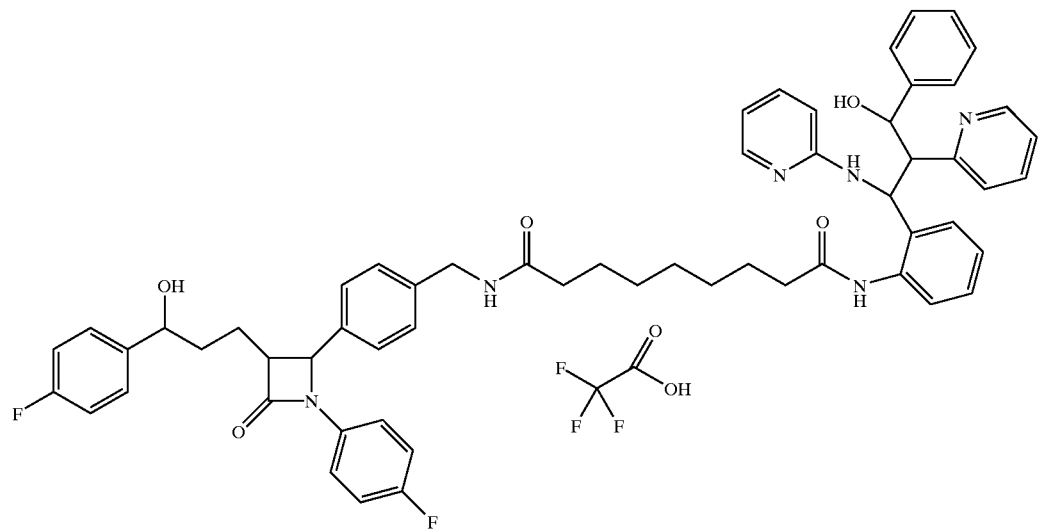

b) (1-{2-[8-(4-{1-(4-Fluorophenyl)-3-[3-(4-fluorophenyl)-3-hydroxypropyl]-4-oxoazetidin-2-yl}benzylcarbamoyl)octanoylamino]phenyl}-3-hydroxy-3-phenyl-2-pyridin-2-ylpropyl)pyridin-2-ylammonium trifluoroacetate (27)

$C_{61}H_{61}F_5N_6O_7$ (1085.19) MS (ESI) 971 (M+H)

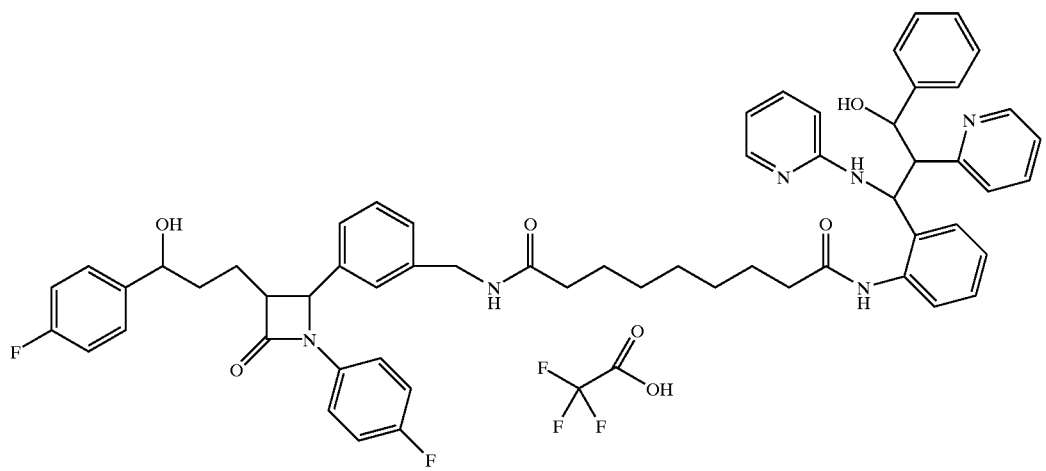
(1-{2-[8-(3-{1-(4-Fluorophenyl)-3-[3-(4-fluorophenyl)-3-hydroxypropyl]-4-oxoazetidin-2-yl}benzylcarbamoyl)octanoylamino]phenyl}-3-hydroxy-3-phenyl-2-pyridin-2-ylpropyl)pyridin-2-ylammonium trifluoroacetate (28)
$C_{61}H_{61}F_5N_6O_7$ (1085.19) MS (ESI) 971 (M+H)
EXAMPLE XV
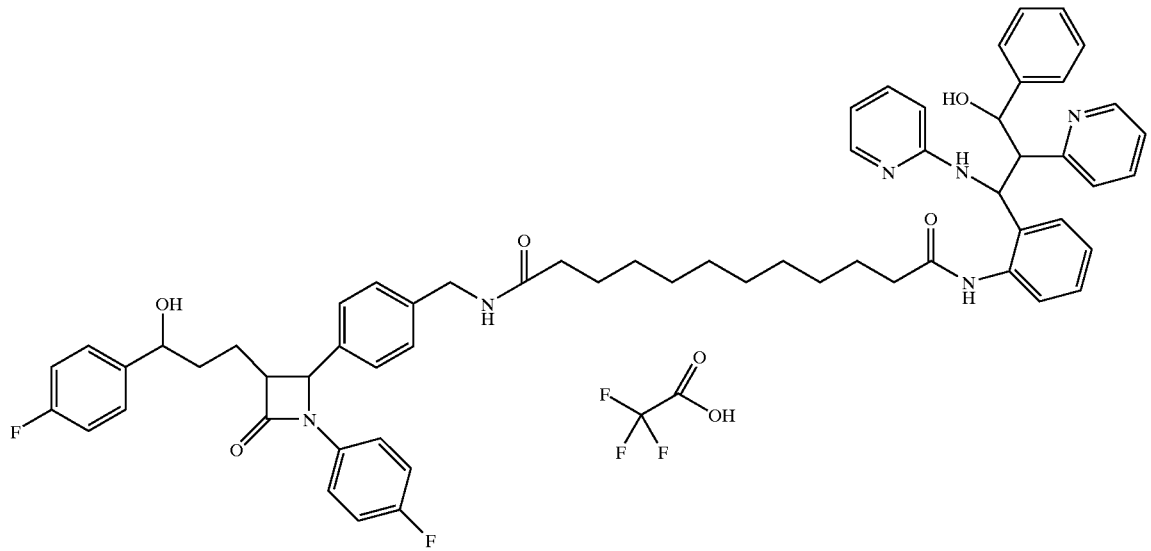

(1-{2-[11-(4-{1-(4-Fluorophenyl)-3-[3-(4-fluorophenyl)-3-hydroxypropyl]-4-oxoazetidin-2-yl}benzylcarbamoyl)undecanoylamino]phenyl}-3-hydroxy-3-phenyl-2-pyridin-2-ylpropyl)pyridin-2-ylammonium trifluoroacetate (30)

EXAMPLE XVI

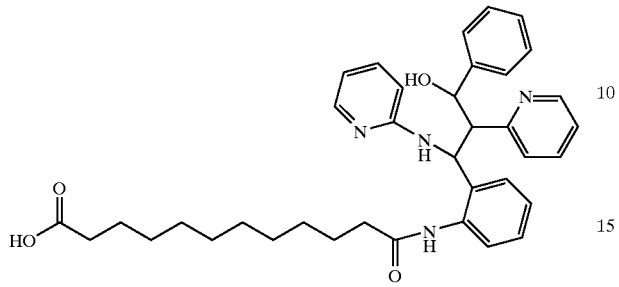

a) 11-{2-[3-Hydroxy-3-phenyl-2-pyridin-2-yl-1-(pyridin-2-ylamino)propyl]phenylcarbamoyl}undecanoic acid (29)

$C_{37}H_{44}N_4O_4$ (608.82) MS (ESI) 609 (M+H)

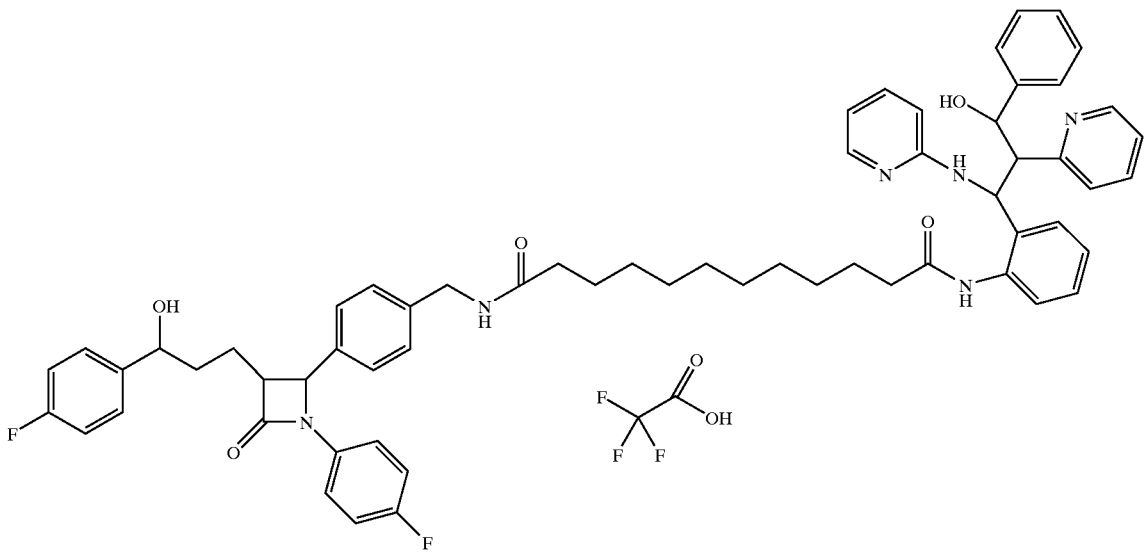

b) (1-{2-[11-(4-{1-(4-Fluorophenyl)-3-[3-(4-fluorophenyl)-3-hydroxypropyl]-4-oxoazetidin-2-yl}benzylcarbamoyl)undecanoylamino]phenyl}-3-hydroxy-3-phenyl-2-pyridin-2-ylpropyl)pyridin-2-ylammonium trifluoroacetate (30)

$C_{64}H_{67}F_5N_6O_7$ (1127.28) MS (ESI) 1013 (M+H)

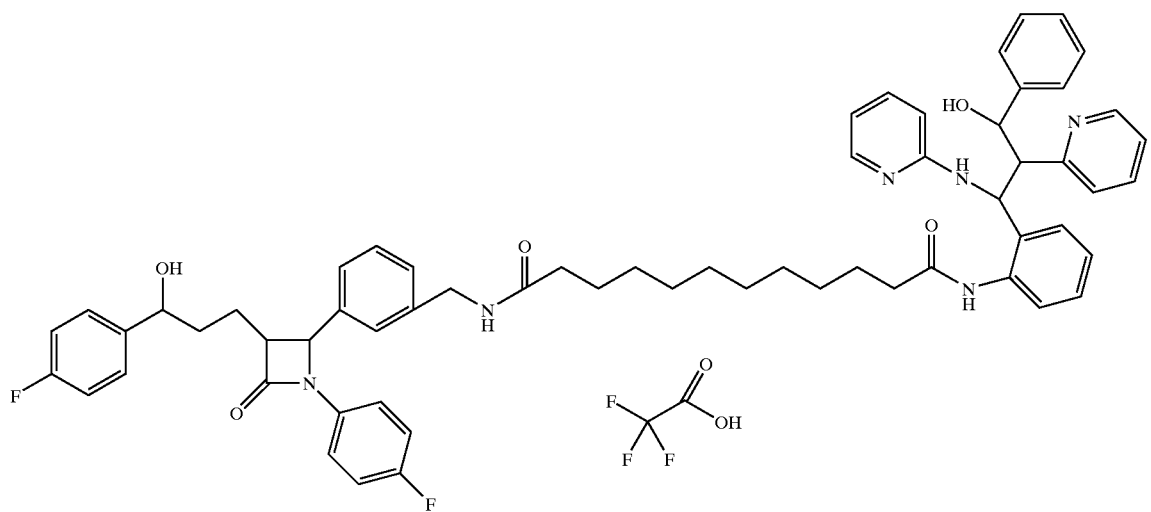
(1-{2-[11-(3-{1-(4-Fluorophenyl)-3-[3-(4-fluorophenyl)-3-hydroxypropyl]-4-oxoazetidin-2-yl}benzylcarbamoyl)undecanoylamino]phenyl}-3-hydroxy-3-phenyl-2-pyridin-2-ylpropyl)pyridin-2-yl ammonium trifluoroacetate (31)
$C_{64}H_{67}F_5N_6O_7$ (1127.28) MS (ESI) 1013 (M+H)
EXAMPLE XVII
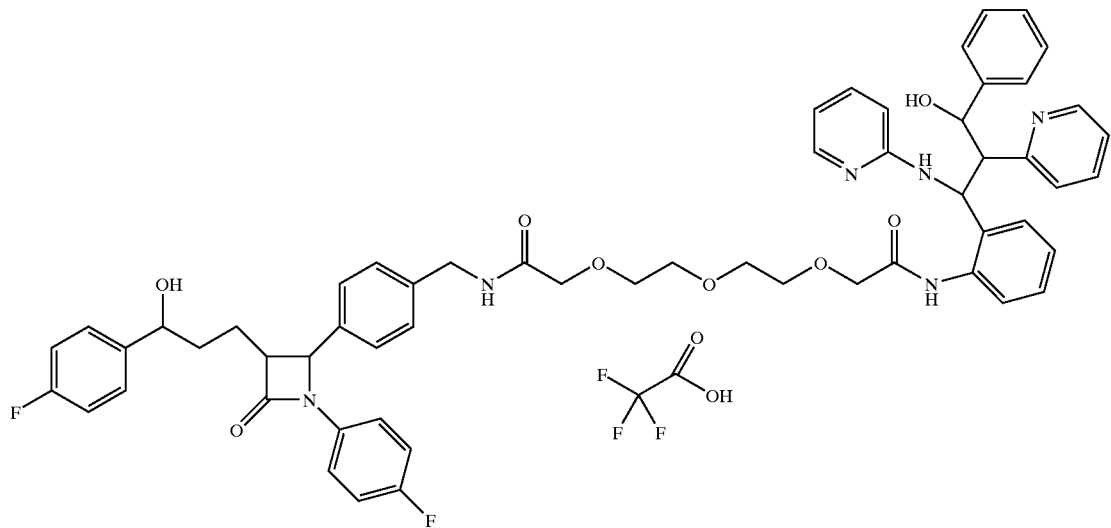

(1-{2-[2-(2-{2-[(4-{1-(4-Fluorophenyl)-3-[3-(4-fluorophenyl)-3-hydroxy-propyl]-4-oxoazetidin-2-yl}benzylcarbamoyl)methoxy]ethoxy}ethoxy)acetylamino]phenyl}-3-hydroxy-3-phenyl-2-pyridin-2-ylpropyl)pyridin-2-ylammonium trifluoroacetate (33)

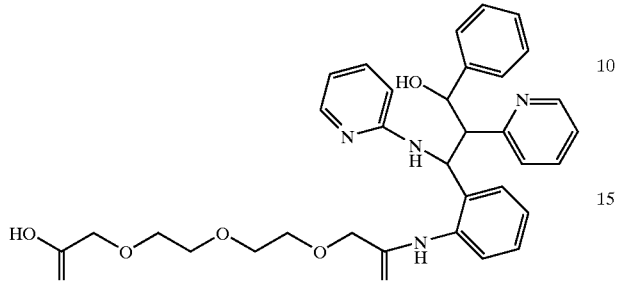

a) {2-[2-({2-[3-Hydroxy-3-phenyl-2-pyridin-2-yl-1-(pyridin-2-ylamino)propyl]phenylcarbamoyl}methoxy)ethoxy]ethoxy}acetic acid (32)

$C_{33}H_{36}N_4O_7$ (600.68) MS (ESI) 591 (M+H)

EXAMPLE XVIII

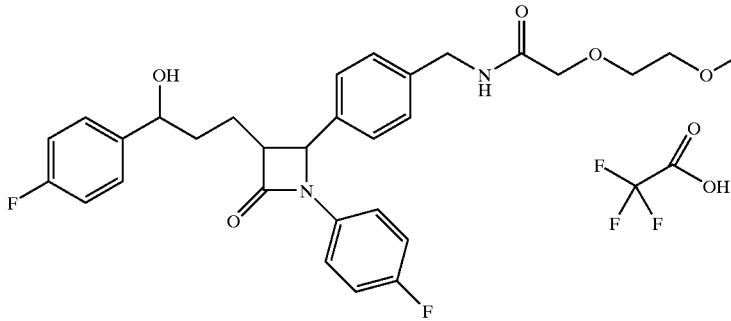

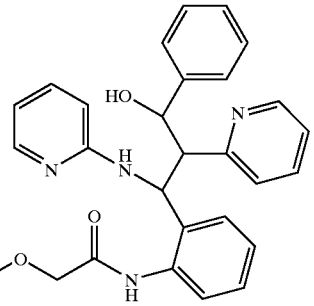

b) (1-{2-[2-(2-{2-[(4-{1-(4-Fluorophenyl)-3-[3-(4-fluorophenyl)-3-hydroxypropyl]-4-oxoazetidin-2-yl}benzylcarbamoyl)methoxy]ethoxy}ethoxy)acetylamino]phenyl}-3-hydroxy-3-phenyl-2-pyridin-2-ylpropyl)pyridin-2-yl-ammonium trifluoroacetate (33)

$C_{60}H_{59}F_5N_6O_{10}$ (1119.17) MS (ESI) 1005 (M+H)

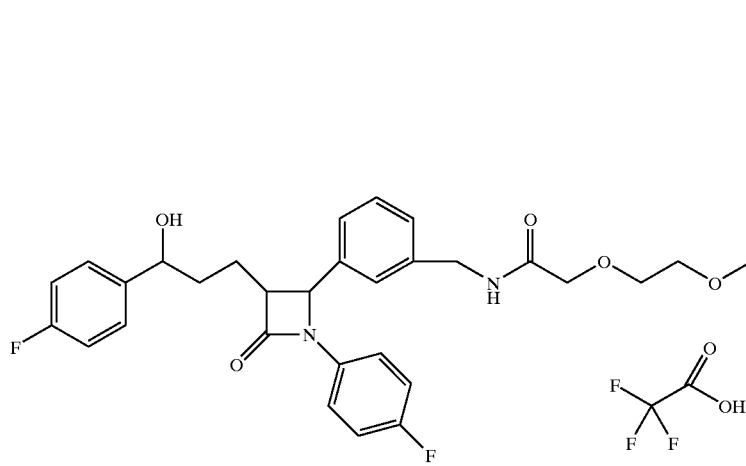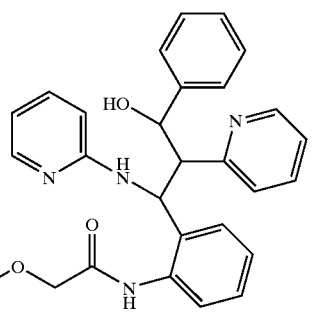
(1-{2-[2-(2-{2-[(3-{1-(4-Fluorophenyl)-3-[3-(4-fluorophenyl)-3-hydroxypropyl]-4-oxoazetidin-2-yl}benzylcarbamoyl)methoxy]ethoxy}ethoxy)acetylamino]phenyl}-3-hydroxy-3-phenyl-2-pyridin-2-ylpropyl)pyridin-2-ylammonium trifluoroacetate (34)
$C_{60}H_{59}F_5N_6O_{10}$ (1119.17) MS (ESI) 1005 (M+H)
EXAMPLE XIX
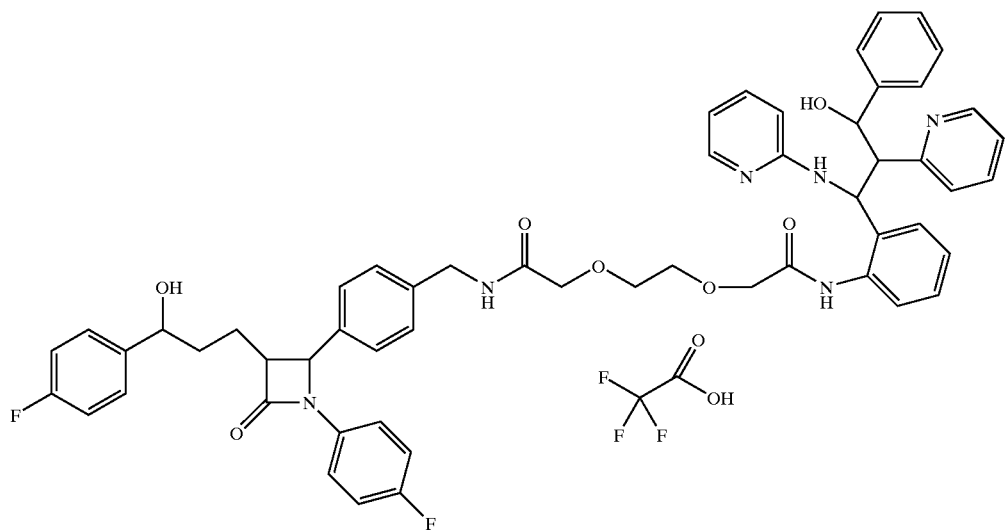

{1-[2-(2-{2-[(4-{1-(4-Fluorophenyl)-3-[3-(4-fluorophenyl)-3-hydroxypropyl]-4-oxoazetidin-2-yl}benzylcarbamoyl)methoxy]ethoxy}acetylamino)phenyl]-3-hydroxy-3-phenyl-2-pyridin-2-ylpropyl}pyridin-2-ylammonium trifluoroacetate 36

EXAMPLE XX

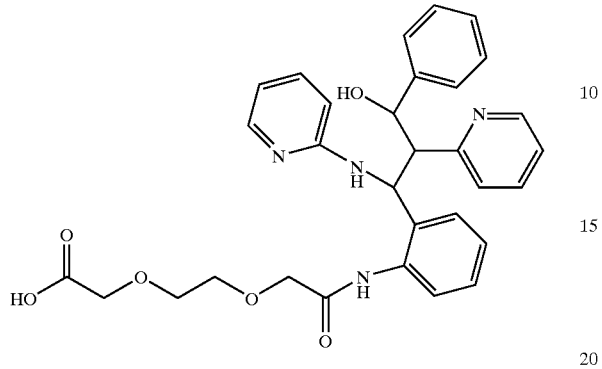

$C_{31}H_{32}N_4O_6$ (556.62) MS (ESI) 557 (M+H)

a) 2-({2-[3-Hydroxy-3-phenyl-2-pyridin-2-yl-1-(pyridin-2-ylamino)propyl]phenylcarbamoyl}methoxy)ethoxy]acetic acid (35)

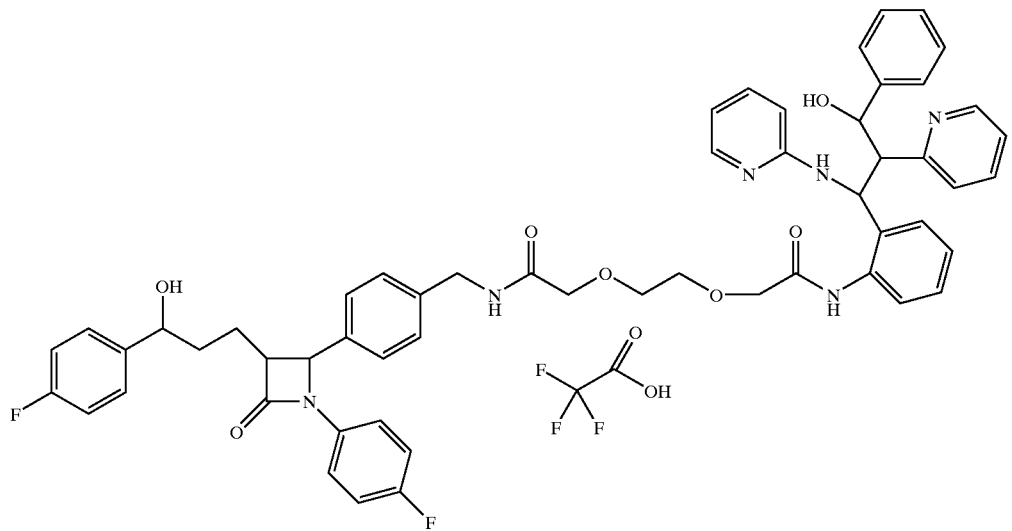

b) {1-[2-(2-{2-[(4-{1-(4-Fluorophenyl)-3-[3-(4-fluorophenyl)-3-hydroxypropyl]-4-oxoazetidin-2-yl}benzylcarbamoyl)methoxy]ethoxy}acetylamino)phenyl]-3-hydroxy-3-phenyl-2-pyridin-2-ylpropyl}pyridin-2-ylammonium trifluoroacetate (36)

$C_{58}H_{55}F_5N_6O_9$ (1075.1 1) MS (ESI) 961 (M+H)

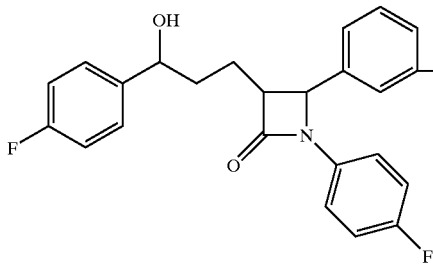
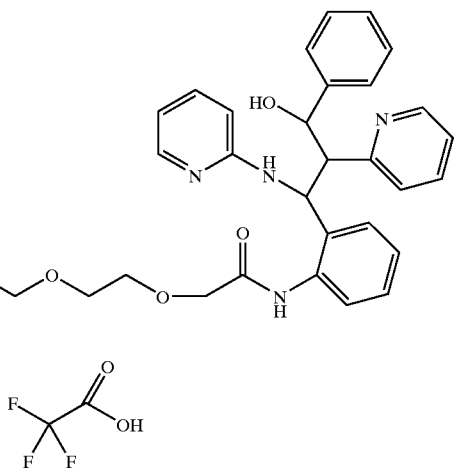

{1-[2-(2-{2-[(3-{1-(4-Fluorophenyl)-3-[3-(4-fluorophenyl)-3-hydroxypropyl]-4-oxoazetidin-2-yl}benzylcarbamoyl)methoxy]ethoxy}acetylamino)phenyl]-3-hydroxy-3-phenyl-2-pyridin-2-ylpropyl}pyridin-2-ylammonium trifluoroacetate (37)

$C_{58}H_{55}F_5N_6O_9$ (1075.1 1) MS (ESI) 961 (M+H)

Using the method described below, the activity of the compounds of the formula I according to the invention was examined:

Effect on Cholesterol Absorption+$^3$H-taurocholic Acid Excretion Using Fecal Excrement of Mice, Rats or Hamsters NMRI mice, Wistar rats, or Golden Syrian hamsters (in groups of n=4–6) are kept in metabolic cages, where they are fed with a standard diet (Altromin, Lage (Lippe)). The afternoon prior to the administration of the radioactive tracers ($^{14}$C-cholesterol), the feed is removed and the animals are adapted to grates.

Additionally, the animals are labeled s.c. with $^3$H-TCA (taurocholic acid) (for example 1 µCi/mouse up to 5 µCi/rat) 24 hours prior to the peroral administration of the test meal ($^{14}$C-cholesterol in Intralipid® 20, Pharmacia-Upjohn).

Cholesterol absorption test: 0.25 ml/mouse Intralipid® 20 (Pharmacia-Upjohn) ((spiked with 0.25 µCi of $^{14}$C-cholesterol in 0.1 mg of cholesterol) is administered perorally by gavage.

Test substances are prepared separately in 0.5% methylcellulose (Sigma)/5% Solutol (BASF, Ludwigshafen) or a suitable vehicle.

The administration volume of the test substance is 0.5 ml/mouse. The test substance is administered immediately prior to the test meal (Intralipid labeled with $^{14}$C-cholesterol) (cholesterol absorption test).

The feces are collected over a period of 24 h: fecal elimination of $^{14}$C-cholesterol and $^3$H-taurocholic acid (TCA) is determined after 24 hours.

The livers are removed and homogenized, and aliquots are incinerated in an oximate (Model 307, Packard) to determine the amount of $^{14}$C-cholesterol which had been taken up/absorbed.

Evaluation:

Feces Samples:

The total weight is determined, the sample is made up with water to a defined volume and then homogenized, and an aliquot is evaporated to dryness and incinerated in an oximate (Model 307 from Packard for the incineration of radioactively labeled samples): the amount of radioactive $^3$H—H$_2$O and $^{14}$C—CO$_2$ is extrapolated to the amount of $^3$H-taurocholic acid and $^{14}$C-cholesterol, respectively, that is excreted (dual isotope technique). The $ED_{200}$ values as dose from a dose-effect curve are interpolated as those doses at which the excretion of TCA or cholesterol is doubled, based on a control group treated at the same time.

Liver Samples:

The amount of $^{14}$C-cholesterol taken up by the liver is based on the administered dose. The $ED_{50}$ values are interpolated from a dose-effect curve as the dose at which the uptake of $^{14}$C-cholesterol by the liver is halved (50%), based on a control group.

The $ED_{50}$ values below demonstrate the activity of the compounds of the formula I according to the invention

| Example No. | $ED_{50}$ (liver) [mg/mouse] |
|---|---|
| XVI | 0.03 |
| XVIII | 0.3 |
| XIX | 0.1 |

As can be seen from the table, the compounds of the formula I have very good cholesterol-lowering action. The compounds can thus be used to control cholesterol concentration. Such control can be by lowering the cholesterol concentration, or maintaining a desired level of cholesterol concentration.

Bioabsorption:

The bioabsorption of the compounds of the formula I can be examined using the Caco cell model (A. R. Hilgers et al., Caco-2 cell monolayers as a model for drug transport across the intestinal mucosa, Pharm. Res. 1990, 7, 902).

Below is a bioabsorption measurement for a reference compound

| | Reference structure | Example |
|---|---|---|
| Apparent partition coefficient $P_{app}$ [cm/s] (according to Lit. Hilgers) | $4.88 \times 10^{-06}$ | |
| Estimated human bioabsorption | 100% | |

| Reference structure | Example |
|---|---|
| Reference structure: Ezetimibe | 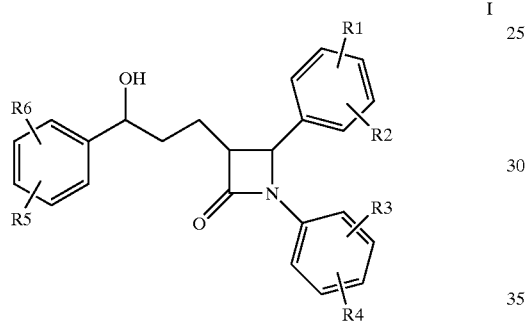 |

We claim:
1. A compound of the formula I,

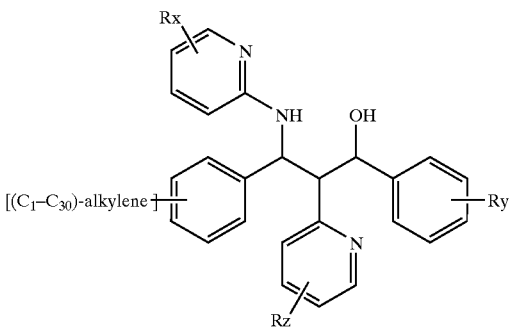

or a pharmaceutically acceptable salt or ester thereof, in which

R1, R2, R3, R4, R5, R6 independently of one another are -L or ($C_1$–$C_{30}$)-alkylene-L, where one or more carbon atoms of the alkylene radical may be replaced by —O—, —(C=O)—, —CH=CH—, —C≡C—, —N(($C_1$–$C_6$)-alkyl)- or —NH—, or H, F, Cl, Br, I, $CF_3$, $NO_2$, CN, COOH, COO($C_1$–$C_6$)-alkyl, $CONH_2$, CONH($C_1$–$C_6$)-alkyl, CON[($C_1$–$C_6$)-alkyl]$_2$, ($C_1$–$C_6$)-alkyl, ($C_2$–$C_6$)-alkenyl, ($C_2$–$C_6$)-alkynyl or O—($C_1$–$C_6$)-alkyl, where one, more or all hydrogens in the alkyl radicals may be replaced by fluorine; or $SO_2$—$NH_2$, $SO_2$NH($C_1$–$C_6$)-alkyl, $SO_2$N[($C_1$–$C_6$)-alkyl]$_2$, S—($C_1$–$C_6$)-alkyl, S—$(CH_2)_n$-phenyl, SO—($C_1$–$C_6$)-alkyl, SO—$(CH_2)_n$-phenyl, $SO_2$—($C_1$–$C_6$)-alkyl or $SO_2$—$(CH_2)_n$-phenyl, where n=0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$; or $NH_2$, NH—($C_1$–$C_6$)-alkyl, N(($C_1$–$C_6$)-alkyl)$_2$, NH($C_1$–$C_7$)-acyl, phenyl or O—$(CH_2)_n$-phenyl, where n=0–6, where the phenyl ring may be mono- to trisubstituted by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_c$, COOH, COO—($C_1$–$C_6$)-alkyl or $CONH_2$;

L is shown connected to ($C_1$–$C_{30}$) as follows:

Rx, Ry, Rz independently of one another are H, F, Cl, Br, I, $CF_3$, $NO_2$, CN, COOH, COO—($C_1$–$C_6$)-alkyl, $CONH_2$, CONH—($C_1$–$C_6$)-alkyl, CON—[($C_1$–$C_6$)-alkyl]$_2$, ($C_1$–$C_6$)-alkyl, ($C_2$–$C_6$)-alkenyl, ($C_2$–$C_6$)-alkynyl or O—($C_1$–$C_6$)-alkyl, where one, more or all hydrogens in the alkyl radicals may be replaced by fluorine; or $SO_2$—$NH_2$, $SO_2$NH—($C_1$–$C_6$)-alkyl, $SO_2$N—[($C_1$–$C_6$)-alkyl]$_2$, S—($C_1$–$C_6$)-alkyl, S—$(CH_2)_n$-phenyl, SO—($C_1$–$C_6$)-alkyl, SO—$(CH_2)_n$-phenyl, $SO_2$—($C_1$–$C_6$)-alkyl or $SO_2$—$(CH_2)_n$-phenyl, where n=0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$; or $NH_2$, NH—($C_1$–$C_6$)-alkyl, N—(($C_1$–$C_6$)-alkyl)$_2$, NH—($C_1$–$C_7$)-acyl, phenyl or O—$(CH_2)_n$-phenyl, where n=0–6, where the phenyl ring may be mono- to trisubstituted by F, Cl, Br, I, OH, $CF_3$, $NO_2$, CN, $OCF_3$, O—($C_1$–$C_6$)-alkyl, ($C_1$–$C_6$)-alkyl, $NH_2$, NH—($C_1$–$C_6$)-alkyl, N—(($C_1$–$C_6$)-alkyl)$_2$, $SO_2$—$CH_3$, COOH, COO—($C_1$–$C_6$)-alkyl or $CONH_2$;

wherein at least one of the radicals R1 to R6 has the meaning -L or ($C_1$–$C_{30}$)-alkylene-L, where one or more carbon atoms of the alkylene radical may be replaced by —O—, —(C=O)—, —CH=CH—, —C≡C—, —N(($C_1$–$C_6$)-alkyl)-, or —NH—.

2. A compound as claimed in claim 1, wherein

R1, R2, R3, R4, R5, R6 independently of one another are -L ($C_1$–$C_{30}$)-alkylene-L, where one or more carbon atoms of the alkylene radical may be replaced by —O—, —(C=O)— or —NH—, or H, F, Cl, Br, I, $CF_3$, $NO_2$, CN, COOH, COO($C_1$–$C_6$)-alkyl, $CONH_2$, CONH($C_1$–$C_6$)-alkyl, CON[($C_1$–$C_6$)-alkyl]$_2$, ($C_1$–$C_6$)-alkyl, ($C_2$–$C_6$)-alkenyl, ($C_2$–$C_6$)-alkynyl or O—($C_1$–$C_6$)-alkyl, where one, more or all hydrogens in the alkyl radicals may be replaced by fluorine; or $SO_2$-$NH_2$, $SO_2$NH($C_1$–$C_6$)-alkyl, $SO_2$N[($C_1$–$C_6$)-alkyl]$_2$, S—($C_1$–$C_6$)-alkyl, S—$(CH_2)_n$-phenyl, SO—($C_1$–$C_6$)-alkyl, SO—$(CH_2)_n$-phenyl, $SO_2$—($C_1$–$C_6$)-alkyl or $SO_2$—$(CH_2)_n$-phenyl, where n=0–6 and the phenyl radical may be substituted up to two times by F, Cl, Br, OH, $CF_3$, $NO_2$, CN, $OCF_3$, O—($C_1$–$C_6$)-alkyl, ($C_1$–$C_6$)-alkyl or $NH_2$; or $NH_2$, NH—($C_1$–$C_6$)-alkyl, N(($C_1$–$C_6$)-alkyl)$_2$, NH($C_1$–$C_7$)-acyl, phenyl or O—$(CH_2)_n$-phenyl, where n=0–6 and the phenyl ring may be mono- to trisubstituted by F, Cl, Br, I, OH, $CF_3$, $NO_2$, CN, $OCF_3$, O—($C_1$–$C_6$)-alkyl, ($C_1$–$C_6$)-alkyl, $NH_2$, NH($C_1$–$C_6$)-alkyl, N(($C_1$–$C_6$)-alkyl)$_2$, $SO_2$—$CH_3$, COOH, COO—($C_1$–$C_6$)-alkyl or $CONH_2$;

L is shown connected to $(C_1-C_{30})$-alkylene as follows:

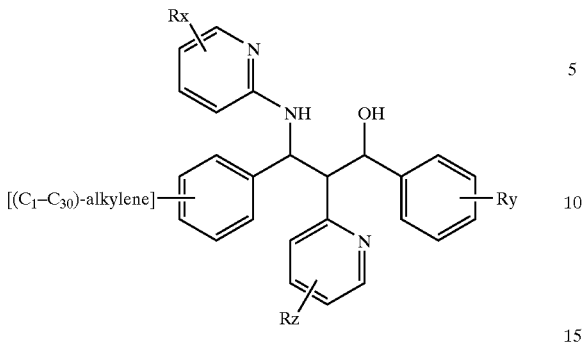

Rx, Ry, Rz independently of one another are H, F, Cl, Br, I, $CF_3$, $NO_2$, CN, COOH, COO—$(C_1-C_6)$-alkyl, $CONH_2$, CONH—$(C_1-C_6)$-alkyl, CON—[$(C_1-C_6)$-alkyl]$_2$, $(C_1-C_6)$-alkyl, $(C_2-C_6)$-alkenyl, $(C_2-C_6)$-alkynyl or O—$(C_1-C_6)$-alkyl, where one, more or all hydrogens in the alkyl radicals may be replaced by fluorine; or $SO_2$—$NH_2$, $SO_2NH$—$(C_1-C_6)$-alkyl, $SO_2N$—[$(C_1-C_6)$-alkyl]$_2$, S—$(C_1-C_6)$-alkyl, S—$(CH_2)_n$-phenyl, SO—$(C_1-C_6)$-alkyl, SO—$(CH_2)_n$-phenyl, $SO_2$—$(C_1-C_6)$-alkyl or $SO_2$—$(CH_2)_n$-phenyl, where n=0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl or $NH_2$; or $NH_2$, NH—$(C_1-C_6)$-alkyl, N—($(C_1-C_6)$-alkyl)$_2$, NH—$(C_1-C_7)$-acyl, phenyl or O—$(CH_2)_n$-phenyl, where n=0–6, where the phenyl ring may be mono- to trisubstituted by F, Cl, Br, I, OH, $CF_3$, $NO_2$, CN, $OCF_3$, O—$(C_1-C_6)$-alkyl, $(C_1-C_6)$-alkyl, $NH_2$, NH—$(C_1-C_6)$-alkyl, N—($(C_1-C_6)$-alkyl)$_2$, $SO_2$—$CH_3$, COOH, COO—$(C_1-C_6)$-alkyl or $CONH_2$;

wherein at least one of the radicals R1 to R6 has the meaning -L $(C_1-C_{30})$-alkylene-L, where one or more carbon atoms of the alkylene radical may be replaced by —O—, —(C=O)— or —NH—.

3. A compound as claimed in claim 1, wherein

R1, R2, R3, R4, R5, R6 independently of one another are -L $(C_1-C_{30})$-alkylene-L, where one or more carbon atoms of the alkylene radical may be replaced by —O—, —(C=O)— or —NH—, or H, F, Cl, Br, I, $CF_3$, $NO_2$, CN, COOH, $COO(C_1-C_6)$-alkyl, $CONH_2$, $CONH(C_1-C_6)$-alkyl, CON [$(C_1-C_6)$-alkyl]$_2$, $(C_1-C_6)$-alkyl, $(C_2-C_6)$-alkenyl, $(C_2-C_6)$-alkynyl or O—$(C_1-C_6)$-alkyl, where one, more or all hydrogens in the alkyl radicals may be replaced by fluorine; or $SO_2$—$NH_2$, $SO_2NH(C_1-C_6)$-alkyl, $SO_2N[(C_1-C_6)$-alkyl]$_2$, S—$(C_1-C_6)$-alkyl, S—$(CH_2)_n$-phenyl, SO—$(C_1-C_6)$-alkyl, SO—$(CH_2)_n$-phenyl, $SO_2$—$(C_1-C_6)$-alkyl or $SO_2$—$(CH_2)_n$-phenyl, where n=0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl or $NH_2$; or $NH_2$, NH—$(C_1-C_6)$-alkyl, N($(C_1-C_6)$-alkyl)$_2$, $NH(C_1-C_7)$-acyl, phenyl or O—$(CH_2)_n$-phenyl, where n=0–6 and the phenyl ring may be mono- to trisubstituted by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, N($(C_1-C_6)$-alkyl)$_2$, $SO_2$—$CH_3$, COOH, COO—$(C_1-C_6)$-alkyl or $CONH_2$;

L is shown connected to $(C_1-C_{30})$-alkylene as follows:

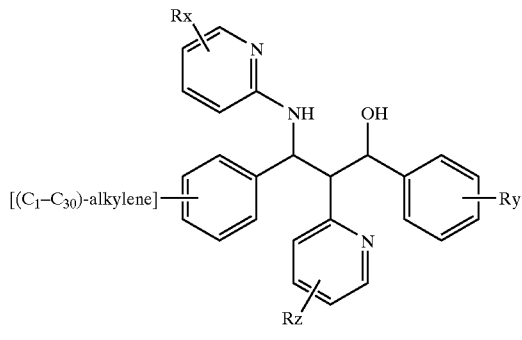

Rx, Ry, Rz independently of one another are H, F, Cl, Br, I, $CF_3$, $NO_2$, CN, COOH, COO—$(C_1-C_6)$-alkyl, $CONH_2$, CONH—$(C_1-C_6)$-alkyl, CON—[$(C_1-C_6)$-alkyl]$_2$, $(C_1-C_6)$-alkyl, $(C_2-C_6)$-alkenyl, $(C_2-C_6)$-alkynyl or O—$(C_1-C_6)$-alkyl, where one, more or all hydrogens in the alkyl radicals may be replaced by fluorine; or $SO_2$—$NH_2$, $SO_2NH$—$(C_1-C_6)$-alkyl, $SO_2N$—[$(C_1-C_6)$-alkyl]$_2$, S—$(C_1-C_6)$-alkyl, S—$(CH_2)_n$-phenyl, SO—$(C_1-C_6)$-alkyl, SO—$(CH_2)_n$-phenyl, $SO_2$—$(C_1-C_6)$-alkyl or $SO_2$—$(CH_2)_n$-phenyl, where n=0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl or $NH_2$; or $NH_2$, NH—$(C_1-C_6)$-alkyl, N—($(C_1-C_6)$-alkyl)$_2$, NH—$(C_1-C_7)$-acyl, phenyl or O—$(CH_2)_n$-phenyl, where n=0–6, where the phenyl ring may be mono- to trisubstituted by F, Cl, Br, I, OH, $CF_3$, $NO_2$, CN, $OCF_3$, O—$(C_1-C_6)$-alkyl, $(C_1-C_6)$-alkyl, $NH_2$, NH—$(C_1-C_6)$-alkyl, N—($(C_1-C_6)$-alkyl)$_2$, $SO_2$—$CH_3$, COOH, COO—$(C_1-C_6)$-alkyl or $CONH_2$;

where one of the radicals R1 or R3 has the meaning $(C_1-C_{30})$-alkylene-L, where one or more carbon atoms of the alkylene radical may be replaced by —O—, —(C=O)— or —NH—.

4. A compound as claimed in claim 1, wherein

R1, R2, R3, R4, R5, R6 independently of one another are —$(CH_2)_{0-1}$—NH—$(C=O)_{0-1}$—$(C_3-C_{25})$-alkylene-$(C=O)_{0-1}$—NH—L, where one or more carbon atoms of the alkylene radical may be replaced by oxygen atoms, or H, F, Cl, Br, I, $CF_3$, $NO_2$, CN, COOH, $COO(C_1-C_6)$-alkyl, $CONH_2$, $CONH(C_1-C_6)$-alkyl, CON [$(C_1-C_6)$-alkyl]$_2$, $(C_1-C_6)$-alkyl, $(C_2-C_6)$-alkenyl, $(C_2-C_6)$-alkynyl or O—$(C_1-C_6)$-alkyl, where one, more or all hydrogens in the alkyl radicals may be replaced by fluorine; or $SO_2$—$NH_2$, $SO_2NH(C_1-C_6)$-alkyl, $SO_2N[(C_1-C_6)$-alkyl]$_2$, S—$(C_1-C_6)$-alkyl, S—$(CH_2)_n$-phenyl, SO—$(C_1-C_6)$-alkyl, SO—$(CH_2)_n$-phenyl, $SO_2$—$(C_1-C_6)$-alkyl or $SO_2$—$(CH_2)_n$-phenyl, where n=0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl or $NH_2$; or $NH_2$, NH—$(C_1-C_6)$-alkyl, N($(C_1-C_6)$-alkyl)$_2$, $NH(C_1-C_7)$-acyl, phenyl or O—$(CH_2)_n$-phenyl, where n=0–6 and the phenyl ring may be mono- to trisubstituted by F, Cl, Br, I, OH, $CF_3$, $NO_2$, CN, $OCF_3$, O—$(C_1-C_6)$-alkyl, $(C_1-C_6)$-alkyl, $NH_2$, $NH(C_1-C_6)$-alkyl, N($(C_1-C_6)$-alkyl)$_2$, $SO_2$—$CH_3$, COOH, COO—$(C_1-C_6)$-alkyl or $CONH_2$;

L as follows:

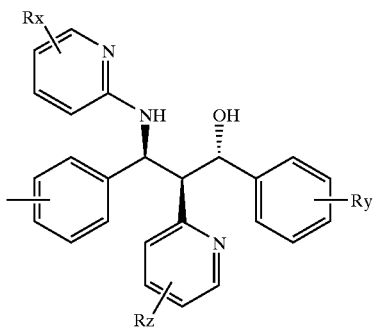

Rx, Ry, Rz independently of one another are H, F, Cl, Br, I, $CF_3$, $NO_2$, CN, COOH, COO—$(C_1-C_6)$-alkyl, $CONH_2$, CONH—$(C_1-C_6)$-alkyl, CON—$[(C_1-C_6)$-alkyl$]_2$, $(C_1-C_6)$-alkyl, $(C_2-C_6)$-alkenyl, $(C_2-C_6)$-alkynyl or O—$(C_1-C_6)$-alkyl, where one, more or all hydrogens in the alkyl radicals may be replaced by fluorine; or $SO_2$—$NH_2$, $SO_2NH$—$(C_1-C_6)$-alkyl, $SO_2N$—$[(C_1-C_6)$-alkyl$]_2$, S—$(C_1-C_6)$-alkyl, S—$(CH_2)_n$-phenyl, SO—$(C_1-C_6)$-alkyl, SO—$(CH_2)_n$-phenyl, $SO_2$—$(C_1-C_6)$-alkyl or $SO_2$—$(CH_2)_n$-phenyl, where n=0–6 and the phenyl radical may be substituted up to two times by F, Cl, Br, OH, $CF_3$, $NO_2$, CN, $OCF_3$, O—$(C_1-C_6)$-alkyl, $(C_1-C_6)$-alkyl or $NH_2$; or $NH_2$, NH—$(C_1-C_6)$-alkyl, N—$((C_1-C_6)$-alkyl$)_2$, NH—$(C_1-C_7)$-acyl, phenyl or O—$(CH_2)_n$-phenyl, where n=0–6, where the phenyl ring may be mono- to trisubstituted by F, Cl, Br, I, OH, $CF_3$, $NO_2$, CN, $OCF_3$, O—$(C_1-C_6)$-alkyl, $(C_1-C_6)$-alkyl, $NH_2$, NH—$(C_1-C_6)$-alkyl, N—$((C_1-C_6)$-alkyl$)_2$, $SO_2$—$CH_3$, COOH, COO—$(C_1-C_6)$-alkyl or $CONH_2$;

where one of the radicals R1 or R3 has the meaning —$(CH_2)_{0-1}$—NH—$(C=O)_{0-1}$—$(C_3-C_{25})$-alkylene-$(C=O)_{0-1}$—NH—L, where one or more carbon atoms of the alkylene radical may be replaced by oxygen atoms.

5. A pharmaceutical composition comprising one or more of the compounds as claimed in claim 1 and a pharmaceutically acceptable carrier.

6. A method for the treatment of impaired lipid metabolism, which comprises administering to a host in need of the treatment an effective amount of at least one compound as claimed in claim 1.

7. A method for lowering or maintaining the serum cholesterol controlling in a host, which comprises administering to the host in need of the lowering or maintaining of serum cholesterol concentration an effective amount of at least one compound as claimed in claim 1.

8. A method for the treatment of an arteriosclerotic manifestation or insulin resistance, which comprises administering to a host in need of the treatment an effective amount of at least one compound as claimed in claim 1.

9. A method as claimed in claim 6, wherein the host suffers from hyperlipidemia.

10. A method as claimed in claim 8, wherein the host suffers from an arteriosclerotic manifestation.

11. A method as claimed in claim 8, wherein the host suffers from insulin resistance.

\* \* \* \* \*